(12) United States Patent
Parker et al.

(10) Patent No.: US 7,258,902 B2
(45) Date of Patent: Aug. 21, 2007

(54) CHIRAL 3,4-DIHYDRO-2H-PYRAN COMPOUNDS

(75) Inventors: Robert Parker, Mannheim (DE); Frank Prechtl, Frankfurt (DE); Sylke Haremza, Neckargemuend (DE); Frank Meyer, Heidelberg (DE); Volkmar Vill, Hamburg (DE); Gunnar Gesekus, Hamburg (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 184 days.

(21) Appl. No.: 10/518,389

(22) PCT Filed: Jun. 30, 2003

(86) PCT No.: PCT/EP03/06885

§ 371 (c)(1),
(2), (4) Date: Dec. 30, 2004

(87) PCT Pub. No.: WO2004/002979

PCT Pub. Date: Jan. 8, 2004

(65) Prior Publication Data

US 2005/0230660 A1  Oct. 20, 2005

(30) Foreign Application Priority Data

Jul. 1, 2002 (DE) .................. 102 29 530

(51) Int. Cl.
| C09K 19/58 | (2006.01) |
| C09K 19/38 | (2006.01) |
| G02B 5/30 | (2006.01) |
| C07D 309/16 | (2006.01) |

(52) U.S. Cl. .................. 428/1.1; 428/1.3; 428/1.31; 252/299.01; 252/299.2; 549/417; 549/420

(58) Field of Classification Search ........... 252/299.01, 252/299.61, 299.62, 299.64, 299.65, 299.66, 252/299.67, 299.2; 428/1.1, 1.3, 1.31; 549/419, 549/416, 417, 420, 421, 425, 426, 427
See application file for complete search history.

(56) References Cited

FOREIGN PATENT DOCUMENTS

| DE | 196 28 700 | 1/1998 |
| DE | 196 40 618 | 4/1998 |
| DE | 198 35 730 | 2/1999 |
| EP | 0 630 892 | 12/1994 |
| EP | 0 931 110 | 7/1999 |
| WO | 95 22586 | 8/1995 |
| WO | 95 24454 | 9/1995 |
| WO | 95 24455 | 9/1995 |
| WO | 96 02597 | 2/1996 |
| WO | 96 04351 | 2/1996 |
| WO | 96 24647 | 8/1996 |
| WO | 97 00600 | 1/1997 |
| WO | 97 27251 | 7/1997 |
| WO | 97 27252 | 7/1997 |
| WO | 97 34862 | 9/1997 |
| WO | 98 47979 | 10/1998 |
| WO | 99 11733 | 3/1999 |
| WO | 99 19267 | 4/1999 |
| WO | 00 47694 | 8/2000 |

OTHER PUBLICATIONS

CAPLUS 1969: 524819.*
Wu, S.-L. et al. "Synthesis and Characterization of Ferroelectric and Antiferroelectric Liquid Crystals Derived from (2S)-2-(6-Hydroxy-2-Naphthyl)Propionic Acid", Mol. Cryst. Liq. Cryst., vol. 264, pp. 39-50 1995.
Liang, J.C. et al. "The Synthesis and Liquid Crystal Behavior of p-Benzotrifluoride Compounds II", Mol. Cryst. Liq. Cryst., vol. 167, pp. 253-258 1989.
Nomura, Elsaku et al. "Synthesis and Conformational Property of Tannin-like p-tert-Butylcalix[4]arene 1,3-Diesters Stabilized by Intramolecular Hydrogen Bonds", J. Org. Chem., vol. 66, pp. 8030-8036 2001.

* cited by examiner

*Primary Examiner*—Shean C Wu
(74) *Attorney, Agent, or Firm*—Oblon, Spivak, McClelland, Maier & Neustadt, P.C.

(57) ABSTRACT

The invention relates to chiral 3,4-dihydro-2H-pyran compounds and diastereomers thereof, and to the use of these compounds as chiral dopants for liquid-crystalline systems.

The invention furthermore relates to non-polymerizable or polymerizable liquid-crystalline compositions which comprise at least one chiral 3,4-dihydro-2H-pyran compound according to the invention, to the use of these non-polymerizable or polymerizable liquid-crystalline compositions for the production of optical components, to the use of the polymerizable liquid-crystalline compositions for printing or coating substrates, for the preparation or production of dispersions and emulsions, films or pigments and optical components of this type, printed or coated substrates, dispersions and emulsions, films and pigments.

20 Claims, No Drawings

CHIRAL 3,4-DIHYDRO-2H-PYRAN COMPOUNDS

The present invention relates to chiral 3,4-dihydro-2H-pyran compounds and diastereomers thereof, and to the use of these compounds as chiral dopants for liquid-crystalline systems.

The present invention furthermore relates to non-polymerizable or polymerizable liquid-crystalline compositions which comprise at least one chiral 3,4-dihydro-2H-pyran compound according to the invention, to the use of these non-polymerizable or polymerizable liquid-crystalline compositions for the production of optical components, to the use of the polymerizable liquid-crystalline compositions for printing or coating substances, for the preparation of dispersions and emulsions, films or pigments, and to optical components, printed or coated substrates, dispersions and emulsions, films and pigments of this type.

Cholesteric liquid-crystal mixtures are usually prepared using a liquid-crystalline (nematic) base material and one or more optically active dopants. This enables the optical properties of the mixture to be varied by simply changing the ratio of nematic to dopant. However, in order to keep the possible adverse effects of the dopant on the other properties of the nematic host system, such as, for example, phase behavior and width, as small as possible, there is a demand, in particular, for dopants which effect large changes in the optical properties even when added in small amounts.

Chiral dopants for liquid-crystalline phases are known in large number from the scientific and patent literature. It is all the more surprising that chiral 3,4-dihydro-2H-pyran compounds have apparently not yet been considered as dopants for liquid-crystalline systems.

It is an object of the present invention to provide further chiral compounds which are suitable for the preparation of cholesteric liquid-crystalline compositions, have a relatively high twisting power and accordingly exhibit a considerable influence on the optical properties of the liquid-crystalline host system, even in comparatively small amounts.

We have found that this object is achieved by the chiral compounds of the general formula I

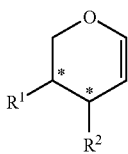

(I)

and diastereomers thereof.

In this formula, $R^1$ and $R^2$, independently of one another, are P—$Y^1$-$A^1$—$Y^2$M-$Y^3$-$(A^2)_m$—$Y^4$— groups, where $A^1$ and $A^2$ are spacers having from one to 30 carbon atoms, M is a mesogenic group, $Y^1$, $Y^2$, $Y^3$ and $Y^4$ are a single chemical bond, —O—, —S—, —CO—, —CO—O—, —O—CO—, —CO—N(R)—, —(R)N—CO—, —O—CO—O—, —O—CO—N(R)—, —(R)N—CO—O— or —(R)N—CO—N(R)—, R is hydrogen or $C_1$-$C_4$-alkyl, P is hydrogen, $C_1$-$C_{12}$-alkyl, a group which is polymerizable or suitable for polymerization, or a radical which carries a group which is polymerizable or suitable for polymerization, and m is a value of 0 or 1, where the variables $A^1$, $A^2$, $Y^1$, $Y^2$, $Y^3$, $Y^4$, M, P and the index m in the groups $R^1$ and $R^2$ may be identical or different, with the proviso that, in the case where the index m is 0, at least one of the variables $Y^3$ and $Y^4$ adjacent to $A^2$ is a chemical bond.

Suitable spacers $A^1$ and $A^2$ are all groups known to the person skilled in the art for this purpose. In general, the spacers contain from one to 30, preferably from one to 12, particularly preferably from one to six, carbon atoms and consist predominantly of linear aliphatic groups. They may be interrupted in the chain, for example by non-adjacent oxygen or sulfur atoms or imino or alkylimino groups, for example methylimino groups.

Possible substituents for the spacer chain are also fluorine, chlorine, bromine, cyano, methyl and ethyl.

Examples of representative spacers are the following:

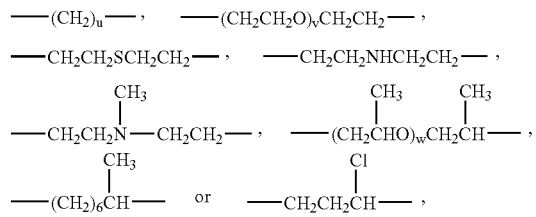

where u is from 1 to 30, preferably from 1 to 12, v is from 1 to 14, preferably from 1 to 5, and w is from 1 to 9, preferably from 1 to 3.

Preferred spacers are ethylene, propylene, n-butylene, n-pentylene and n-hexylene.

The mesogenic groups M can be all groups which are suitable as such to the person skilled in the art.

Particularly suitable are mesogenic groups of the formula Ia $$(-T-Y^5)_r-T-$$ Ia where the variables have the following meanings:

T is a divalent saturated or unsaturated carbocyclic or heterocyclic radical, $Y^5$ is a chemical bond, —O—, —S—, —CO—, —CO—O—, —O—CO—, —CO—N(R)—, —(R)N—CO—, —O—CO—O—, —O—CO—N(R)—, —(R)N—CO—O— or —(R)N—CO—N(R)—, and r has a value of 0, 1, 2 or 3, where, for r>0, both the variables T and the variables $Y^5$ may in each case be identical to or different from one another.

The radicals T may be ring systems which are substituted by fluorine, chlorine, bromine, cyano, hydroxyl, formyl, nitro, $C_1$-$C_{20}$-alkyl, $C_1$-$C_{20}$-alkoxy, $C_1$-$C_{20}$-alkoxycarbonyl, $C_1$-$C_{20}$-monoalkylaminocarbonyl, $C_1$-$C_{20}$-alkylcarbonyl, $C_1$-$C_{20}$-alkylcarbonyloxy or $C_1$-$C_{20}$-alkylcarbonylamino.

Preferred radicals T are the following:

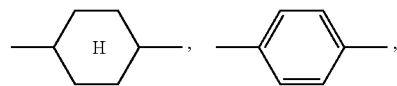

Examples of suitable mesogenic groups M are the following:

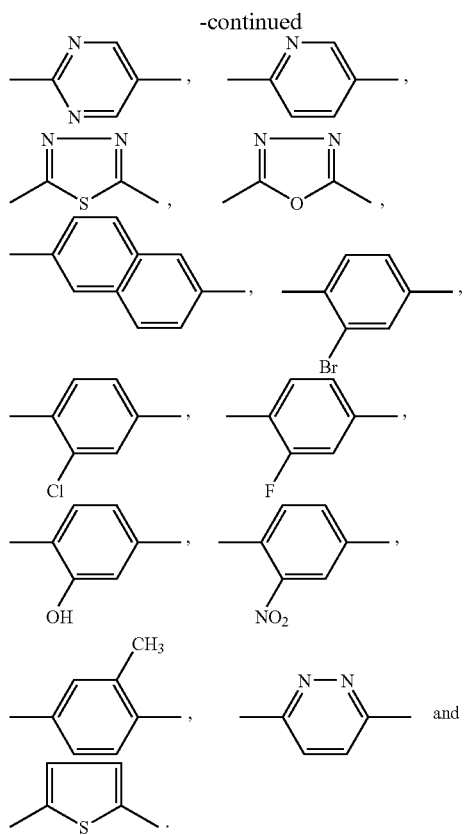

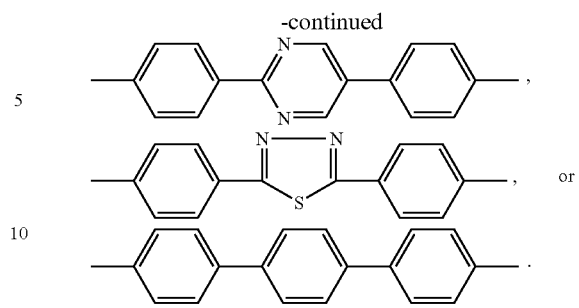

Other possible mesogenic groups M correspond to the following formulae:

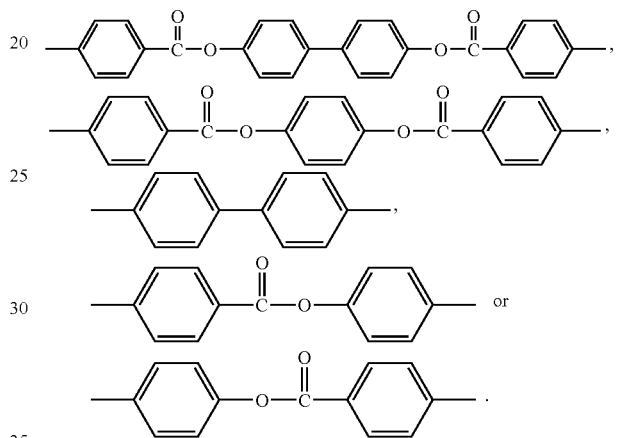

The (unsubstituted) mesogenic groups indicated above may of course, corresponding to the abovementioned examples of possible radicals T, also be substituted by fluorine, chlorine, bromine, cyano, hydroxyl, formyl, nitro, $C_1$-$C_{20}$-alkyl, $C_1$-$C_{20}$-alkoxy, $C_1$-$C_{20}$-alkoxycarbonyl, $C_1$-$C_{20}$-monoalkylaminocarbonyl, $C_1$-$C_{20}$-alkylcarbonyl, $C_1$-$C_{20}$-alkylcarbonyloxy or $C_1$-$C_{20}$-alkylcarbonylamino. Preferred substituents are, in particular, short-chain aliphatic radicals, such as methyl, ethyl, n-propyl, i-propyl, n-butyl, i-butyl, sec-butyl, tert-butyl, and alkoxy, alkoxycarbonyl, alkylcarbonyl, alkylcarbonyloxy, alkylcarbonylamino and monoalkylaminocarbonyl radicals which contain these alkyl groups.

Preferred 3,4-dihydro-2H-pyran compounds here are those in which the index r in the mesogenic group of the formula Ia in the groups $R^1$ and $R^2$ adopts, independently of one another, the value 0 or 1.

In particular, mesogenic groups in the groups $R^1$ and $R^2$ that may be mentioned are the following:

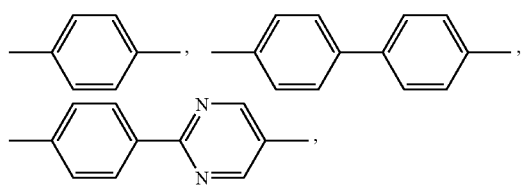

-continued

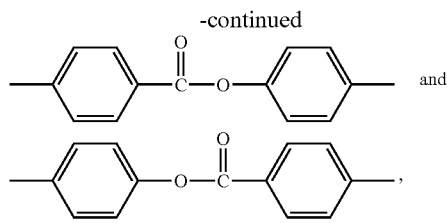

and

Furthermore, these mesogenic groups, as mentioned above, may additionally be substituted.

$C_1$-$C_{12}$-alkyl radicals which may be mentioned for P are branched or unbranched $C_1$-$C_{12}$-alkyl chains, for example methyl, ethyl, n-propyl, 1-methylethyl, n-butyl, 1-methylpropyl-, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl, n-octyl, 2-ethylhexyl, n-nonyl, n-decyl, n-undecyl and n-dodecyl.

Preferred alkyl radicals for P are the branched or unbranched $C_1$-$C_6$-alkyl chains, for example methyl, ethyl, n-propyl, 1-methylethyl, n-butyl, 1-methylpropyl-, 2-methylpropyl, 1,1-dimethylethyl, n-pentyl, 1-methylbutyl, 2-methylbutyl, 3-methylbutyl, 2,2-dimethylpropyl, 1-ethylpropyl and n-hexyl.

Suitable groups which are polymerizable or suitable for polymerization or suitable radicals which carry a group which is polymerizable or suitable for polymerization (such groups are also referred to below as "reactive radicals") for P are the following:

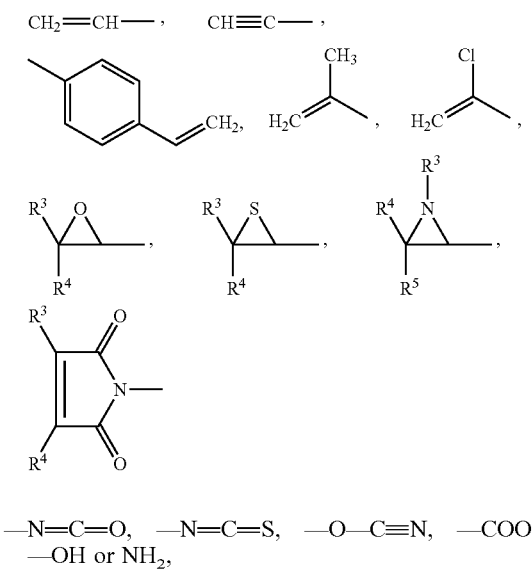

—N=C=O, —N=C=S, —O—C≡N, —COOH, —OH or $NH_2$, where the radicals $R^3$ to $R^5$ may be identical or different and are hydrogen or $C_1$-$C_4$-alkyl, such as methyl, ethyl, n-propyl, isopropyl, n-butyl, isobutyl, sec-butyl or tert-butyl.

Of the polymerizable groups, the cyanates can trimerize spontaneously to give cyanurates. The other groups mentioned require further compounds containing complementary reactive groups for polymerization. Thus, for example, isocyanates can polymerize with urethanes and with amines to give urea derivatives. An analogous situation applies to thiiranes and aziridines. Carboxyl groups can condense to form polyesters and polyamides. The maleimido group is particularly suitable for free-radical copolymerization with olefinic compounds, for example styrene or compounds containing styrene structural units.

The complementary reactive radicals here, together with the reactive radicals corresponding to them, may be present in one and the same 3,4-dihydro-2H-pyran compound according to the invention (meaning that this compound can potentially also polymerize with itself) or in a further 3,4-dihydro-2H-pyran compound according to the invention. However, these complementary reactive radicals may also, together with the corresponding reactive radicals, be present in one and the same (auxiliary) compounds or in further (auxiliary) compounds of this type.

Polymerizable groups which should be particularly emphasized are the acrylate, methacrylate and vinyl radicals.

In accordance with the invention, the compounds of the formula I and their preferred embodiments are used as chiral dopants for liquid-crystalline systems. The term "liquid-crystalline systems" here is not restricted only to systems in which one or more constituents already have liquid-crystalline properties per se (in the temperature range of interest) and are also present in the system, but instead is also taken to mean systems in which liquid-crystalline behavior does not manifest itself until the components are mixed or alternatively until the chiral compound(s) according to the invention is/are admixed (for example lyotropic systems). It should furthermore be noted here that the compounds according to the invention need not necessarily already have liquid-crystalline behavior themselves.

Also claimed are liquid-crystalline and polymerizable liquid-crystalline compositions which comprise at least one chiral compound of the formula I or a preferred embodiment.

The term "liquid-crystalline compositions" here is taken to mean, in particular, non-polymerizable compositions which are not capable of forming polymerization or condensation products under conventional conditions. These compositions can be prepared, for example, by mixing suitable, commercially available liquid-crystalline materials, as used, for example, for active LC layers in display technology, with one or more of the compounds according to the invention. In the latter compounds, P in the formula I accordingly corresponds to hydrogen or $C_1$-$C_{12}$-alkyl.

The use of these (non-polymerizable) liquid-crystalline compositions for the production of optical components, for example LCDs, is claimed in accordance with the invention. Optical components obtained in this way are likewise claimed in accordance with the invention.

The present invention furthermore relates to polymerizable liquid-crystalline compositions. These are taken to mean, in particular, compositions in which at least one of the constituents is capable of forming polymerization or condensation products under conventional conditions.

Depending on the number of reactive radicals in the constituents of these compositions, the desired degree of polymerization, crosslinking and/or condensation can be set after polymerization or condensation has taken place. The compounds of the formula I according to the invention in such compositions have at least one, preferably two, reactive radicals P in the groups $R^1$ and/or $R^2$. These compounds can easily be prepared by mixing suitable polymerizable, liquid-crystalline materials with one or more of the compounds according to the invention. Suitable polymerizable, liquid-crystalline compounds are described, for example, in WO 95/22586, 95/24454, 95/24455, 96/04351, 96/24647, 97/00600, 97/34862 and 98/47979 and DE-A 198 35 730 and essentially correspond to the schematic structure P-Y-A-Y-M-Y-A-Y-P, where the variables P, Y, A and M have analogous definitions to the variables P, $Y^1$ to $Y^4$, $A^1$, $A^2$ and M in the formula I.

The use of these polymerizable liquid-crystalline compositions for the production of optical components, for example polarizers or filters, is claimed in accordance with the invention.

The present invention also relates to optical components of this type which have been obtained using these polymerizable liquid-crystalline compositions according to the invention.

The polymerizable liquid-crystalline compounds claimed are used in accordance with the invention for printing or coating substrates. In this case, these compositions may also comprise further additives. Suitable such additives are those selected from the group consisting of photoinitiators, reactive diluents and diluents, additives selected from the group consisting of antifoams and deaerators, lubricants and flow auxiliaries, thermally curing or radiation-curing auxiliaries, substrate wetting auxiliaries, wetting and dispersion aids, hydrophobicizing agents, adhesion promoters and auxiliaries for improving the scratch resistance, additives selected from the group consisting of dyes and pigments, and additives selected from the group consisting of light, heat and/or oxidation stabilizers.

The chemical/physical nature of these additives is discussed in detail in the specification WO 00/47694. Also described therein are liquid-crystalline mixtures, as which the polymerizable liquid-crystalline compositions according to the invention, if desired mixed with the abovementioned additives, should also be described. The polymerizable liquid-crystalline compositions claimed in the present application, if desired mixed with said additives, can accordingly be employed as printing and coating compositions for substrates, as stated in the specification WO 00/47694.

Furthermore, printed or coated substrates which have been produced using the polymerizable compositions according to the invention, if desired mixed with the abovementioned additives, are furthermore claimed as part of the present invention Suitable such substrates, besides paper and board products, for example for carrier bags, newspapers, brochures, gift packaging and packaging materials for utility, semi-luxury and luxury products, are also films, for example for decorative and non-decorative packaging purposes, and textiles of all types and leather.

However, further substrates are also (consumer) electronic products, for example MC, MD, DVD and video recorders, televisions, radios, telephones/cellphones, etc., and computer equipment, products from the leisure, sports, domestic and toy sector, for example bicycles, children's toys, skis, snowboards and surfboards, inline skates and roller-skating and ice-skating boots, and also domestic appliances. In addition, substrates of this type are also taken to mean, for example, writing utensils and spectacle frames.

However, further substrates are also surfaces to be encountered in the construction sector, such as building walls or even window panes. In the latter case, a functional effect may also be desired in addition to a decorative effect. It is thus possible to produce multilayer coatings on the window material, with the individual layers having different chemical/physical properties. For example, if individual layers of the polymerizable liquid-crystalline compositions of opposite twist (through use of the one enantiomer and its optical antipode as dopant in accordance with the present invention) or individual layers of crosslinked, cholesteric liquid-crystalline compositions of the same twist direction, but in each case different pitch and thus different reflection properties (through the use of different concentrations of dopant in accordance with the present invention) are applied, certain wavelengths or wavelength ranges of the light spectrum can be reflected specifically. This facilitates, for example, an IR- or UV-reflecting window coating. Regarding this aspect of the LC compositions according to the invention, especially thermal insulation coatings, reference is also made to the specification WO 99/19267.

Also claimed as part of the present invention is the use of the polymerizable liquid-crystalline compositions according to the invention for the preparation of dispersions and emulsions, preferably based on water. For the preparation of dispersions and emulsions of this type, reference is made to WO 96/02597 and WO 98/47979, in which the preparation of dispersions and emulsions using liquid-crystalline materials is described.

The present invention also relates to dispersions and emulsions of this type which have been prepared using the polymerizable liquid-crystalline compositions according to the invention. These dispersions and emulsions can likewise be used for printing and coating substrates as have already been mentioned above by way of example.

The present invention furthermore relates to the use of the polymerizable liquid-crystalline compositions according to the invention for the production of films. Films of this type are taken to mean, in particular, self-supporting layers, as obtained by polymerization of the compositions. These films may be located on substrates of such a type that it is possible for them to be easily detached and transferred to other substrates to remain there permanently through suitable measures. Such films can be used, for example, in the area of film coating and in lamination processes.

The present invention accordingly also relates to films which have been produced using the polymerizable liquid-crystalline compositions according to the invention.

Also claimed is the use of the polymerizable liquid-crystalline compositions according to the invention for the preparation of pigments.

The preparation of such pigments is known and is described in detail in the specification WO 99/11733. In addition, however, pigments of preset shape and size can be prepared using printing techniques with the aid of meshes in whose interspaces the polymerizable composition are located. The subsequent polymerization or condensation of the polymerizable composition is followed here by detachment or removal of the substrate from the mesh. These procedures are described in detail in the specifications WO 96/02597, WO 97/27251, WO 97/27252 and EP 0 931 110.

The polymerizable liquid-crystalline compositions are converted into polymers having a frozen liquid-crystalline ordered structure with the aid of their reactive groups and, depending on their chemical nature, through condensation or free-radical or ionic polymerization processes, which may be initiated by photochemical reactions.

These pigments may be single-layered (homogeneous) or have a multilayered structure. However, the latter pigments can usually only be prepared if use is made of coating processes in which a plurality of layers are generated successively one on top of the other and subsequently subjected to mechanical comminution.

The present invention thus also relates to pigments prepared from such polymerizable liquid-crystalline compositions according to the invention.

EXAMPLES

A. General

A.I. Chromatographic Methods

All reactions were followed by thin-layer chromatography on ready-made silica-gel plates (Merck, silica gel 60, $F_{254}$). The detection was carried out by UV absorption and spraying with a 10% ethanolic sulfuric acid followed by heat treatment.

Separations by column chromatography were carried out by means of flash chromatography on silica gel (230-400 mesh, particle size 0.040-0.063 mm, Merck) with the distilled mobile phases indicated in each case. Anhydrous solvents were purchased from Fluka under the corresponding quality designation or dried by common methods and stored over freshly activated molecular sieve.

A.II. Analytical Details

Optical rotations: Perkin-Elmer PE 243 or 341 polarimeter at the sodium D line (589 nm), cell length 10 cm, concentration $[c]=[g/100\ ml]$.

NMR spectroscopy: Bruker AMX 200, Bruker AMX 400 or DRX 500 in automatic operation; 1st order evaluation. The internal standard used was TMS, or calibration was carried out to the characteristic solvent signals.

Phase conversions (uncorrected): Olympus BH polarizing microscope with Mettler FP 82 heating stage; liquid-crystalline phase allocation on the basis of characteristic structures.

HTP measurements (HTP=helical twisting power): lens variant of the Grandjean-Cano method, 0.5-6 mol % in ZLI 1840 (commercially available liquid-crystalline product from Merck); HTP data: 15° C. below the clearing point. The sign of the HTP was determined with reference to contact mixtures having cholesteric mesophases of known sign by observation of the nematic compensation line.

The abbreviations C, Ch, BP, N, $S_A$ and I in the determination of the phase conversions stand for crystalline, cholesteric, blue phase, nematic, smectic A phase and isotropic respectively.

A.III. Standard Operating Procedures (SOPs)

SOP-1: Esterification by the DCC Method (DCC: N,N'-dicyclohexylcarbodiimide)

A solution of the alcohol or phenol (1.0 eq.), of the carboxylic acid (1.1 eq.), of N,N'-dicyclohexylcarbodiimide (Aldrich, purity 99%; about 1.1-1.7 eq.) and catalytic amounts of 4-pyrrolidinopyridine (Aldrich, purity 98%; about 0.01 eq.) is stirred in anhydrous dichloromethane until the reaction is complete. The N,N'-dicyclohexylurea formed is filtered off, the solvent is removed under reduced pressure, and the residue is purified as described.

SOP-2: Basic Deacetylation Using Sodium Methoxide

In each case, 1 mmol of the ester is dissolved in 5 ml of absolute methanol, and a catalytic amount of sodium methoxide is added until the mixture is basic. After the mixture has been stirred at room temperature for 12 hours, it is neutralized using acidic ion exchanger (Amberlite IR 120 $H^+$ form) and filtered, and the solvent is removed under reduced pressure.

SOP-3: Esterification by the Imidazolide Method

Firstly, one equivalent of N,N'-carbonyldiimidazole (Aldrich, purity 99%) and one equivalent of the carboxylic acid per equivalent of hydroxyl function to be esterified are gently warmed in 2-5 ml of anhydrous N,N-dimethylformamide under a nitrogen atmosphere with evolution of $CO_2$. Depending on the carboxylic acid, the reaction is complete after 5-120 minutes (solution 1). A catalytic amount of sodium is then added at room temperature under a nitrogen atmosphere to a solution 2 of 1 mmol of the alcohol in 2 ml of anhydrous N,N-dimethylformamide. When the sodium has completely dissolved, this solution is added dropwise under a nitrogen atmosphere to the solution 1, prepared at the beginning, of the carboxylic acid imidazolide, and, if necessary, the mixture is warmed with stirring to from 40° C. to a maximum of 80° C., depending on the reaction rate. When the reaction is complete, the solvent is removed under reduced pressure, and the crude product is purified as indicated in each case.

SOP-4: Basic Deacetylation Using Sodium Carbonate

In each case, 1 g of the ester is dissolved in 10 ml of absolute methanol, and 1 g of sodium carbonate is added. After the mixture has been stirred at room temperature for 3-12 hours, the sodium carbonate is filtered off using Celite® (Aldrich), the solution is neutralized using acidic ion exchanger (Amberlite® IR 120 $H^+$ form; Aldrich), and the solvent is removed under reduced pressure.

SOP-5: Esterification of Alcohols and Phenols Using Carboxylic Acid Chlorides

A catalytic amount of 4-pyrrolidinopyridine (about 0.01 eq.) and 1 equivalent of the alcohol or phenol are added under a nitrogen atmosphere to an anhydrous solution of dichloromethane and pyridine 1:1 (in each case 2 ml of solution per 1 mmol of the alcohol or phenol). 1.05 equivalents of the carboxylic acid chloride per hydroxyl function (dissolved in the smallest possible amount of anhydrous dichloromethane) are slowly added dropwise to the batch with stirring. When the reaction is complete, the reaction batch is diluted with dichloromethane and neutralized using 2 M hydrochloric acid solution and washed once with distilled water. The organic phase is dried over magnesium sulfate and evaporated under reduced pressure. The crude product is purified as indicated in each case.

SOP-6: Selective Deprotection of Phenyl Acetates Using Guanidine Hydrochloride 1 mmol of guanidine hydrochloride (Aldrich, purity 99%) is dissolved in 10 ml of anhydrous methanol and stirred for five minutes at room temperature with 0.9 equivalent of sodium methoxide. The mixture is added to a solution of 1 mmol of the phenyl acetate in 50 ml of methanol, and the resultant methyl acetate is removed together with the solvent at 40° C. and 270 mbar on a rotary evaporator. Work-up can be carried out by two methods:

Method 1: The reaction batch is evaporated to dryness under reduced pressure, 50 ml of 1 M hydrochloric acid and 50 ml of dichloromethane are added, and the mixture is stirred until there are no longer any undissolved residues present. The organic phase is separated off, the aqueous phase is extracted a number of times with dichloromethane, the combined organic phases are dried over magnesium sulfate, and the solvent is removed under reduced pressure.

Method 2: The reaction batch is evaporated to dryness under reduced pressure, dissolved in 10 ml of 1,2-dimethoxyethane, acidified with 1 M hydrochloric acid and slowly added with stirring to 100 ml of distilled water. The resultant precipitate is filtered off, dissolved in dichloromethane, and dried over magnesium sulfate, and the solvent is removed under reduced pressure.

B. Synthesis of Glycals from the Pentose Series

Scheme 1:

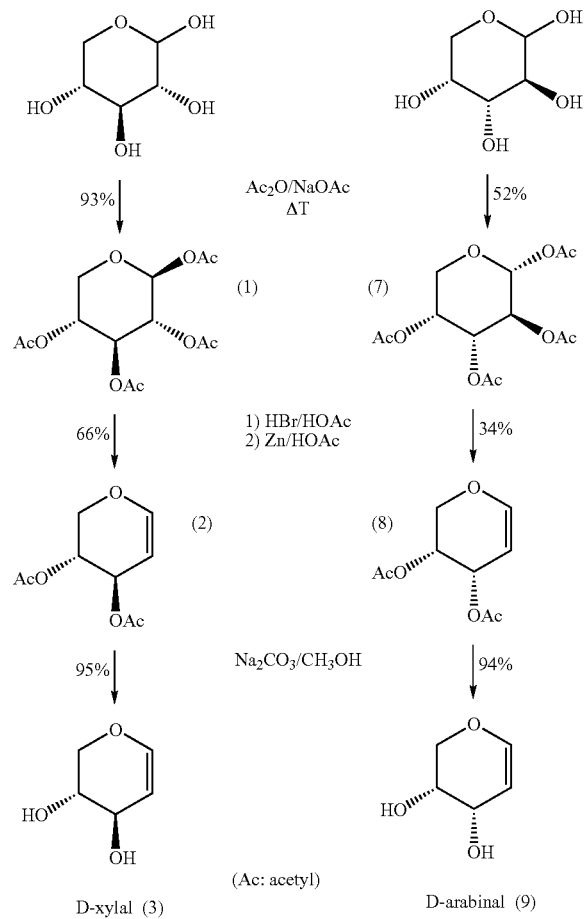

(Ac: acetyl)

B.I. Synthesis of D-xylal (3)

B.I.1. Synthesis of 1,2,3,4-tetra-O-acetyl-β-D-xylopyranose (1)

50.0 g (0.33 mol) of D-xylose (Aldrich, purity 99%) are added in portions at 115° C. after removal of the supply of heat to a stirred suspension of 43 g of sodium acetate in 236 ml of acetic anhydride at such a rate that the temperature does not rise above 118° C. The mixture is then stirred at 115° C. for two hours. After cooling to room temperature, the reaction batch is poured into one liter of ice-water, 500 ml of dichloromethane are added, and the mixture is stirred for 12 hours. The aqueous phase is separated off and extracted three times with 250 ml of dichloromethane each time. The combined organic phases are washed with saturated sodium hydrogencarbonate solution until neutral, rinsed with 250 ml of water and dried over magnesium sulfate. Activated carbon is then added, the mixture is stirred for a quarter of an hour, the activated carbon is filtered off, and the solvent is removed.

Empirical formula: $C_{13}H_{18}O_9$ (MW=318.28 g/mol), yield: 98 g (0.31 mol, 93%); Characterization: colorless crystals; $[\alpha]_D^{20}$=−20.5 (c=0.5, $CHCl_3$); m.p.: 127° C.; the structure was confirmed by $^1$H-NMR (400 MHz, $CDCl_3$) and $^{13}$C-NMR (125 MHz, $CDCl_3$).

B.I.2. Synthesis of 3,4-di-O-acetyl-D-xylal (2)

56.00 g (0.176 mol) of compound 1 are dissolved in 15 ml of acetic anhydride and 15 ml of glacial acetic acid. After cooling to 0° C., 100 ml of hydrogen bromide/glacial acetic acid (33%) are added dropwise, and the mixture is stirred at room temperature for 2 hours. The crude acetobromoxylose solution is added dropwise at 0° C. over the course of 1.5 hours to a reduction mixture comprising 47.48 g of sodium acetate trihydrate, 300 ml of acetone, 80 ml of distilled water, 80 ml of acetic acid and 250 g of activated zinc powder. During this addition, the temperature must not exceed 10° C. When the addition is complete, the mixture is stirred at 0° C. for a further 1 hour and then at room temperature for a further 1.25 hours. After the zinc has been filtered off, the filter residue is washed with an acetic acid/water mixture (1:1). The solution is then extracted once with ice-water and three times with cold chloroform, and the combined organic phases are neutralized using sodium hydrogencarbonate. The solution is dried over magnesium sulfate, and the solvent is removed under reduced pressure. Purification of the product is carried out by flash chromatography with silica-gel filtration (petroleum ether (50/70)/diethyl ether, 3:1).

Empirical formula: $C_9H_{12}O_5$ (MW=200.19 g/mol), yield: 23.47 g (0.117 mol, 66%); Characterization: colorless solid; $[\alpha]_D^{20}$=−316.7 (c=1.0, $CHCl_3$); m.p.: 37-39° C.; the structure was confirmed by $^1$H-NMR (400 MHz, $CDCl_3$) and $^{13}$C-NMR (100 MHz, $CDCl_3$).

B.I.3. Synthesis of D-xylal (3)

Preparation in accordance with SOP-4: 4.00 g of compound 2 (20 mmol) and 4.00 g of anhydrous sodium carbonate in 50 ml of methanol.

Empirical formula: $C_5H_8O_3$ (MW=116.12 g/mol), yield: 2.23 g (19 mmol, 95%); Characterization: yellowish solid; $[\alpha]_D^{20}$=−249.8 (c=0.5, $CHCl_3$); m.p.: 46.0-49.1° C.; the structure was confirmed by $^1$H-NMR (400 MHz, $CD_3OD$) and $^{13}$C-NMR (100 MHz, $CD_3OD$).

B.II. Synthesis of D-arabinal (9)

B.II.1. Synthesis of 1,2,3,4-tetra-O-acetyl-α-D-arabinopyranose (7)

50.00 g (0.33 mol) of D-arabinose (Aldrich, purity 99%) are added in portions at 115° C. after removal of the supply of heat to a stirred suspension of 43 g of sodium acetate in 236 ml of acetic anhydride at such a rate that the temperature does not rise above 118° C. The mixture is then stirred at 115° C. for two hours. After cooling to room temperature, the reaction batch is poured into one liter of ice-water, 500 ml of dichloromethane are added, and the mixture is stirred for 12 hours. The aqueous phase is separated off and extracted three times with 250 ml of dichloromethane each time. The combined organic phases are washed with saturated sodium hydrogencarbonate solution until neutral, rinsed with 250 ml of water and dried over magnesium sulfate. The solvent is subsequently removed under reduced pressure. Purification: multiple recrystallization from ethanol.

Empirical formula: $C_{13}H_{18}O_9$ (MW=318.28 g/mol), yield: 55.03 g (0.17 mol, 52%); Characterization: colorless crystals; $[\alpha]_D^{20}$=−43.1 (c=0.5, $CHCl_3$); m.p.: 94.7° C.; the structure was confirmed by $^1$H-NMR (400 MHz, $CDCl_3$) and $^{13}$C-NMR (100 MHz, $CDCl_3$).

B.II.2. Synthesis of 3,4-di-O-acetyl-D-arabinal (8)

55.00 g (0.173 mol) of compound 7 are dissolved in 15 ml of acetic anhydride and 15 ml of glacial acetic acid. After cooling to 0° C., 100 ml of hydrogen bromide/glacial acetic acid (33%) are added dropwise, and the mixture is stirred at room temperature for 2 hours. The crude acetobromoarabinose solution is added dropwise at 0° C. over the course of 1.5 hours to a reduction mixture comprising 47.48 g of sodium acetate trihydrate, 300 ml of acetone, 80 ml of distilled water, 80 ml of acetic acid and 250 g of activated zinc powder. During this addition, the temperature must not exceed 10° C. When the addition is complete, the mixture is stirred at 0° C. for a further 1 hour and then at room temperature for a further 1.25 hours. After the zinc has been filtered off, the filter residue is washed with an acetic acid/water mixture (1:1). The solution is then extracted once with ice-water and three times with cold chloroform, and the combined organic phases are neutralized using sodium hydrogencarbonate. The solution is dried over magnesium sulfate, and the solvent is removed. The product is purified by flash chromatography with column filtration (petroleum ether (50/70)/diethyl ether, 3:1).

Empirical formula: $C_9H_{12}O_5$ (MW=200.19 g/mol), yield: 11.58 g (58 mmol, 34%); Characterization: viscous syrup; $[\alpha]_D^{20}$=+265.2 (c=1.2, $CHCl_3$); the structure was confirmed by $^1$H-NMR (400 MHz, $CDCl_3$) and $^{13}$C-NMR (125 MHz, $CDCl_3$).

B.II.3. Synthesis of D-arabinal (9)

Preparation in accordance with SOP-2: 5.70 g (28.5 mmol) of compound 8 in 55 ml of anhydrous methanol.

Empirical formula: $C_5H_8O_3$ (MW=116.12 g/mol), yield: 3.10 g (26.7 mmol, 94%); Characterization: colorless crystals; $[\alpha]_D^{20}$=+238.7 (c=0.5, $CH_3OH$); m.p.: 80.7° C.; the structure was confirmed by $^1$H-NMR (400 MHz, $CD_3OD$) and $^{13}$C-NMR (100 MHz, $CD_3OD$).

C. Synthesis of Dopants According to the Invention Based on D-xylal (3) and D-arabinal (9)

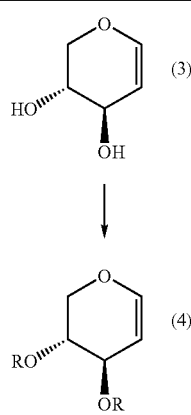

| (4a): | R = $H_{15}C_7O$—Ph—Ph—CO |
| (4b): | R = $H_{15}C_7O$—Ch—Ph—CO |
| (4c): | R = $H_3CO$—Ph—CO |
| (4d): | R = $H_{17}C_8O$—Ph—COO—Ph—CO |

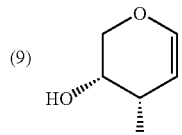

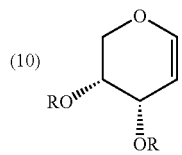

| (10a): | R = $H_3CO$—Ph—CO |
| (10b): | R = $H_{17}C_8O$—Ph—COO—Ph—CO |

(Ph: 1,4-phenylene; Ch: trans-1,4-cyclohexylene)

C.I. Synthesis of Dopants According to the Invention Based on D-xylal (3)

C.I.1. Synthesis of 3,4-di-O-(4"-heptyloxybiphenyl-4'-carbonyl)-D-xylal (4a)

Preparation in accordance with SOP-3. Solution 2 with 122 mg (1.05 mmol) of compound 3 in 2 ml of N,N'-dimethylformamide is added dropwise to solution 1 with 686 mg (2.10 mmol) of 4"-heptyloxybiphenyl-4'-carboxylic acid (synthetic procedure: S.-L. Wu et al., Mol. Cryst. Liq. Cryst. Sci. Technol. Sect. A 1995, 264, 29-50) and 341 mg (2.10 mmol) of N,N-carbonyldiimidazole in 4 ml of anhydrous N,N-dimethylformamide (reaction temperature: 40° C.), reaction temperature 70° C. Purification: distilled water is added to the evaporated crude product, the mixture is filtered, and the residue is washed once with water, dried under reduced pressure and recrystallized from ethanol.

Empirical formula: $C_{45}H_{52}O_7$ (MW=704.91 g/mol), yield: 240 mg (0.34 mmol, 32%); Characterization: colorless solid; $[\alpha]_D^{20}$=−286.0 (c=0.5, $CHCl_3$); C 155.7-156.6 (Ch 147.0 BP) I; calc.: C 76.68 H 7.44, found: C 76.49 H 7.41; the structure was confirmed by $^1$H-NMR (400 MHz, $CDCl_3$) and $^{13}$C-NMR (100 MHz, $CDCl_3$).

C.I.2. Synthesis of 3,4-di-O-(4'-(trans-4"-heptylcyclohexyl)benzoyl)-D-xylal (4b)

Preparation in accordance with SOP-3. Solution 2 with 123 mg (1.06 mmol) of compound 3 in 2 ml of N,N-dimethylformamide is added dropwise to solution 1 with 630 mg (2.08 mmol) of 4'-(trans-4"-heptylcyclohexyl)benzoic acid (synthetic procedure: J. C. Liang, L. Chen, Mol. Cryst. Liq. Cryst. 1989, 167, 253-258) and 340 mg (2.10 mmol) of N,N-carbonyldiimidazole in 4 ml of anhydrous N,N-dimethylformamide (reaction temperature: 40° C.), reaction temperature 65° C. Purification: distilled water is added to the evaporated crude product, the mixture is filtered, and the residue is washed once with water, dried under reduced pressure and recrystallized from ethanol.

Empirical formula: $C_{45}H_{64}O_5$ (MW=685.00 g/mol), yield: 210 mg (0.31 mmol, 29%); Characterization: colorless solid; $[\alpha]_D^{20}$=−218.9 (c=0.5, $CHCl_3$); C 125.4 (Ch<100) I; calc.: C 78.90 H 9.42, found: C 78.95 H 9.51; the structure was confirmed by $^1$H-NMR (400 MHz, $CDCl_3$) and $^{13}$C-NMR (100 MHz, $CDCl_3$).

C.I.3. Synthesis of 3,4-di-o-(4'-methoxybenzoyl)-D-xylal (4c)

Preparation in accordance with SOP-5 with 118 mg (1.02 mmol) of compound 3 in 2 ml of a solution of dichloromethane and pyridine 1:1 and 182 mg (1.07 mmol) of 4-methoxybenzoyl chloride (Aldrich, purity 99%). The crude product is purified by column chromatography on silica gel (eluent: petroleum ether (50/70)/ethyl acetate, 3:1).

Empirical formula: $C_{21}H_{20}O_7$ (MW=384.39 g/mol), yield: 260 mg (0.68 mmol, 67%); Characterization: colorless solid; $[\alpha]_D^{20}$=−372.0 (c=0.5, $CHCl_3$); m.p.: 140.9° C.; calc.: C 65.62 H 5.24, found: C 65.65 H 5.27; the structure was confirmed by $^1$H-NMR (400 MHz, $CDCl_3$) and $^{13}$C-NMR (100 MHz, $CDCl_3$).

C.I.4. Synthesis of 3,4-di-o-(4'-(4''-octyloxybenzoyloxy) benzoyl)-D-xylal (4d)

C.I.4.1. Synthesis of 4-(benzoyloxy)benzoic Acid 17.3 ml (20.90 g, 149 mmol) of benzoyl chloride (Aldrich, purity 99%) are added dropwise over a period of 30 minutes with vigorous stirring to an ice-cooled solution of 20.00 g (145 mmol) of 4-hydroxybenzoic acid (Aldrich, purity 99%) and 12.00 g (300 mmol) of sodium hydroxide in 300 ml of distilled water and 30 ml of acetone. After a further 30 minutes, the mixture is acidified using concentrated hydrochloric acid and diluted with 750 ml of distilled water. The resultant white precipitate is filtered off and recrystallized from methanol/ethanol/ethyl acetate (450 ml+225 ml+300 ml).

Empirical formula: $C_{14}H_{10}O_4$ (MW=242.23 g/mol), yield: 27.01 g (112 mmol, 77%); Characterization: colorless crystals; m.p.: 222.6° C.; the structure was confirmed by $^1$H-NMR (400 MHz, $CDCl_3$).

C.I.4.2. Synthesis of 4-(benzoyloxy)benzoyl chloride 10.00 g (41.3 mmol) of 4-(benzoyloxy)benzoic acid and one drop of N,N-dimethylformamide are refluxed in 40 ml of thionyl chloride with stirring until gas is no longer evolved. The excess thionyl chloride is very substantially removed by distillation under reduced pressure and co-distilled twice with petroleum ether (50/70) under reduced pressure from the remaining residue for complete removal. Purification is carried out by recrystallization from 150 ml of petroleum ether (50/70)/ethyl acetate 2:1, and the crystals are washed with 4 ml of petroleum ether (50/70)

Empirical formula: $C_{14}H_9O_3Cl$ (MW=260.68 g/mol), yield: 7.23 g (27.7 mmol, 67%); Characterization: colorless crystals; m.p.: 134.0° C.; the structure was confirmed by $^1$H-NMR (400 MHz, benzene-$d_6$).

C.I.4.3. Synthesis of 3,4-di-O-(4'-benzoyloxybenzoyl)-D-xylal

Preparation in accordance with SOP-5 with 594 mg (5.12 mmol) of compound 3 in 5 ml of anhydrous pyridine and 2.998 g (11.50 mmol) of 4-(benzoyloxy)benzoyl chloride in 10 ml of anhydrous dichloromethane. The crude product is purified by column chromatography on silica gel (eluent: chloroform).

Empirical formula: $C_{33}H_{24}O_9$ (MW=564.55 g/mol), yield: 333 mg (0.59 mmol, 12%); Characterization: colorless crystals; $[\alpha]_D^{20}$=−285.0 (c=0.2, $CHCl_3$); C 139.2 (Ch 127.9) I; calc.: C 70.21 H 4.28, found: C 70.26 H 4.28; the structure was confirmed by $^1$H-NMR (400 MHz, $CDCl_3$) and $^{13}$C-NMR (100 MHz, $CDCl_3$).

C.I.4.4. Synthesis of 3,4-di-o-(4-acetyloxybenzoyl)-D-xylal

Preparation in accordance with SOP-5 with 3.00 g (25.8 mmol) of compound 3 in 130 ml of dichloromethane and 40 ml of anhydrous pyridine as well as 11.10 g (55.9 mmol) of 4-acetyloxybenzoyl chloride (synthetic procedure: E. Nomura et al., J. Org. Chem. 2001, 66, 8030-8036) in 10 ml of anhydrous dichloromethane. The crude product is recrystallized from 320 ml of ethanol/toluene (7:1).

Empirical formula: $C_{23}H_{20}O_9$ (MW=440.41 g/mol), yield: 9.34 g (21.2 mmol, 82%); Characterization: colorless crystals; $[\alpha]_D^{20}$=−310.1 (c=0.6, $CHCl_3$); m.p.: 145.6° C.; calc.: C 62.73 H 4.58, found: C 62.48 H 4.50; the structure was confirmed by $^1$H-NMR (400 MHz, $CDCl_3$) and $^{13}$C-NMR (100 MHz, $CDCl_3$).

C.I.4.5. Synthesis of 3,4-di-O-(4'-hydroxybenzoyl)-D-xylal

Preparation in accordance with SOP-6 with 5.00 g (11.3 mmol) of 3,4-di-O-(4-acetyloxybenzoyl)-D-xylal in 250 ml of anhydrous methanol as well as 2.10 g (22.0 mmol) of guanidine hydrochloride and 1.07 g (19.8 mmol) of sodium methoxide in 100 ml of anhydrous methanol. Work-up: method 1.

Empirical formula: $C_{19}H_{16}O_7$ (MW=356.33 g/mol), yield: 3.75 g (10.5 mmol, 93%); Characterization: colorless crystals; $[\alpha]_D^{20}$=−363.8 (c=0.5, $CH_3OH$); m.p.: 161.2° C.; calc.: C 64.04 H 4.53, found: C 63.67 H 4.54; the structure was confirmed by $^1$H-NMR (400 MHz, acetone-$d_6$) and $^{13}$C-NMR (100 MHz, acetone-$d_6$).

C.I.4.6. Synthesis of 3,4-di-O-(4'-(4''-octyloxybenzoyloxy) benzoyl)-D-xylal (4d)

Preparation in accordance with SOP-1 400 mg (1.12 mmol) of 3,4-di-O-(4'-hydroxybenzoyl)-D-xylal, 609 mg (2.95 mmol) of DCC and 626 mg (2.50 mmol) of 4-octyloxybenzoic acid in 40 ml of anhydrous dichloromethane. The crude product is recrystallized from 70 ml of isopropanol.

Empirical formula: $C_{49}H_{56}O_{11}$ (MW=820.98 g/mol), yield: 625 mg (0.76 mmol, 68%); Characterization: colorless crystals; $[\alpha]_D^{20}$=−223.8 (c=0.6, $CHCl_3$); C 120.9 Ch decomp.; calc.: C 71.69 H 6.88, found: C 71.37 H 6.96; the structure was confirmed by $^1$H-NMR (400 MHz, $CDCl_3$) and $^{13}$C-NMR (125 MHz, $CDCl_3$).

C.II. Synthesis of Dopants According to the Invention Based on D-arabinal (9)

C.II.1. Synthesis of 3,4-di-O-(4'-methoxybenzoyl)-D-arabinal (10a)

Preparation in accordance with SOP-5 with 3.00 g (25.8 mmol) of compound 9 in 30 ml of anhydrous pyridine and 10.30 g (60.4 mmol) of 4-methoxybenzoyl chloride in 5 ml of anhydrous dichloromethane. The crude product is purified by column chromatography on silica gel (eluent: petroleum ether (50/70)/ethyl acetate, 7:1).

Empirical formula: $C_{21}H_{20}O_7$ (MW=384.39 g/mol), yield: 5.33 g (13.9 mmol, 54%); Characterization: colorless syrup; $[\alpha]_D^{20}$=+281.1 (c=0.5, $CHCl_3$); calc.: C 65.62 H 5.24, found: C 65.71 H 5.30; the structure was confirmed by $^1$H-NMR (400 MHz, $CDCl_3$) and $^{13}$C-NMR (100 MHz, $CDCl_3$).

C.II.2. Synthesis of 3,4-di-o-(4'-(4''-octyloxybenzoyloxy) benzoyl)-D-arabinal (10b)

C.II.2.1. Synthesis of 3,4-di-O-(4'-acetoxybenzoyl)-D-arabinal

Preparation in accordance with SOP-5 with 400 mg (3.44 mmol) of compound 9 in 20 ml of dichloromethane and 7 ml of anhydrous pyridine as well as 1.50 g (7.55 mmol) of 4-acetoxybenzoyl chloride in 1.5 ml of anhydrous dichloromethane.

Empirical formula: $C_{23}H_{20}O_9$ (MW=440.41 g/mol), yield: 1.436 g (3.26 mmol, 95%); Characterization: colorless syrup; $[\alpha]_D^{20}$=−146.7 (c=0.5, CHCl$_3$); calc.: C 62.73 H 4.58, found: C 62.72 H 4.53; the structure was confirmed by $^1$H-NMR (400 MHz, CDCl$_3$) and $^{13}$C-NMR (125 MHz, CDCl$_3$).

C.II.2.2. Synthesis of 3,4-di-O-(4'-hydroxybenzoyl)-D-arabinal

Preparation in accordance with SOP-6 with 1.200 g (2.72 mmol) of 3,4-di-O-(4'-acetoxybenzoyl)-D-arabinal in 160 ml of anhydrous methanol as well as 0.242 g (2.53 mmol) of guanidine hydrochloride and 0.131 g (2.42 mmol) of sodium methoxide in 20 ml of anhydrous methanol. Work-up: method 1.

Empirical formula: $C_{19}H_{16}O_7$ (MW=356.33 g/mol), yield: 950 mg (2.67 mmol, 98%); Characterization: colorless syrup; $[\alpha]_D^{20}$=−108.6 (c=0.7, CHCl$_3$); calc.: C 64.04 H 4.53, found: C 63.51 H 4.52; the structure was confirmed by $^1$H-NMR (400 MHz, acetone-d$_6$) and $^{13}$C-NMR (100 MHz, acetone-d$_6$).

C.II.2.3. Synthesis of 4-octyloxybenzoic Acid 17.64 g (128 mmol) of 4-hydroxybenzoic acid (Aldrich, purity 99%) and 14.32 g (255 mmol) of potassium hydroxide are dissolved in 30 ml of distilled water and added to 260 ml of ethanol. After addition of 33.0 g (29.7 ml, 0.17 mol) of 1-bromooctane (Aldrich, purity 99%), the solution is heated at the boil for 24 hours with stirring. A further 14.32 g (255 mmol) of potassium hydroxide are then added, and the mixture is refluxed with stirring for a further two hours. After the reaction batch has been cooled, the solvent is substantially removed under reduced pressure, and the residue is taken up in distilled water and strongly acidified using 2 M hydrochloric acid solution. The residue is extracted with chloroform, dried over magnesium sulfate, evaporated and recrystallized from acetone.

Empirical formula: $C_{15}H_{22}O_3$ (MW=250.34 g/mol), yield: 26.1 g (104 mmol, 81%); Characterization: colorless crystal needles; C 101 S$_A$ 107 N 146 I; the structure was confirmed by $^1$H-NMR (400 MHz, CDCl$_3$).

C.II.2.4. Synthesis of 3,4-di-O-(4'-(4"-octyloxybenzoyloxy)benzoyl)-D-arabinal (10b)

Preparation in accordance with SOP-1 with 0.788 g (2.21 mmol) of 3,4-di-O-(4'-hydroxybenzoyl)-D-arabinal, 1.240 g (6.01 mmol) of DCC and 1.127 g (4.50 mmol) of 4-octyloxybenzoic acid in 80 ml of anhydrous dichloromethane. The crude product is recrystallized from 40 ml of isopropanol.

Empirical formula: $C_{49}H_{56}O_{11}$ (MW=820.98 g/mol), yield: 1.227 g (1.49 mmol, 67%); Characterization: colorless crystals; $[\alpha]_D^{20}$=+138.5 (c=0.6, CHCl$_3$); m.p.: 75.5-75.9° C.; calc.: C 71.69 H 6.88, found: C 71.42 H 6.97; the structure was confirmed by $^1$H-NMR (400 MHz, CDCl$_3$) and $^{13}$C-NMR (125 MHz, CDCl$_3$).

D. Measurement of the HTP on Selected Dopants According to the Invention

HTP values were determined in ZLI 1840 by the procedure described in A.II. The values obtained are listed in the following table.

| Compound | HTP (in µm$^{-1}$) |
|---|---|
| 4a | +29 |
| 4b | +26 |
| 4c | +30 |

| Compound | HTP (in µm$^{-1}$) |
|---|---|
| 4d | +35 |
| 10a | +13 |
| 10b | +30 |

We claim:

1. A chiral compound of the general formula I

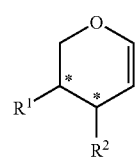

(I)

and diastereomers thereof, where

R$^1$ and R$^2$, independently of one another, are P—Y$^1$-A$^1$-Y$^2$-M-Y$^3$—(A$^2$)$_m$—Y$^4$— groups, wherein A$^1$ and A$^2$ are spacers having one to 30 carbon atoms, M is a mesogenic group, Y$^1$, Y$^2$, Y$^3$ and Y$^4$ are, independently of one another, a single chemical bond, —O—, —S—, —CO—, —CO—O—, —O—CO—, —CO—N(R)—, —(R)N—CO—, —O—CO—O—, —O—CO—N(R)—, —(R)N—CO—O— or —(R)N—CO—N(R)—, R is hydrogen or C$_1$-C$_4$-alkyl, P is hydrogen, C$_1$-C$_{12}$-alkyl, a group which is polymerizable or suitable for polymerization, or a radical which carries a group which is polymerizable or suitable for polymerization, and m is a value of 0 or 1, and wherein the variables A$^1$, A$^2$, Y$^1$, Y$^2$, Y$^3$, Y$^4$, M, P and the index m, in the groups R$^1$ and R$^2$, are identical or different, with the proviso that, in the case where the index m is 0, at least one of the variables Y$^3$ and Y$^4$ adjacent to A$^2$ is a single chemical bond.

2. The compound as claimed in claim 1, wherein the mesogenic group M conforms to the formula Ia (-T-Y$^5$)$_r$-T-     (Ia)

wherein

T is a divalent saturated or unsaturated carbocyclic or heterocyclic radical,

Y$^5$ is a single chemical bond, —O—, —S—, —CO—, —CO—O—, —O—CO—, —CO—N(R)—, —(R)N—CO—, —O—CO—O—, —O—CO—N(R)—, —(R)N—CO—O— or —(R)N—CO—N(R)—, R is hydrogen or C$_1$-C$_4$-alkyl, and r is a value of 0, 1, 2 or 3, where, for r>0, both the variables T and the variables Y$^5$ are, in each case identical to, or different from, one another.

3. The A compound as claimed in claim 2, wherein the index r in the mesogenic group of the formula Ia, in the group R$^1$ and the index r in the mesogenic group of the formula Ia in group R$^2$ are, independently of one another, 0 or 1.

4. The Compound as claimed in claim 2, wherein T is selected from the group consisting of:

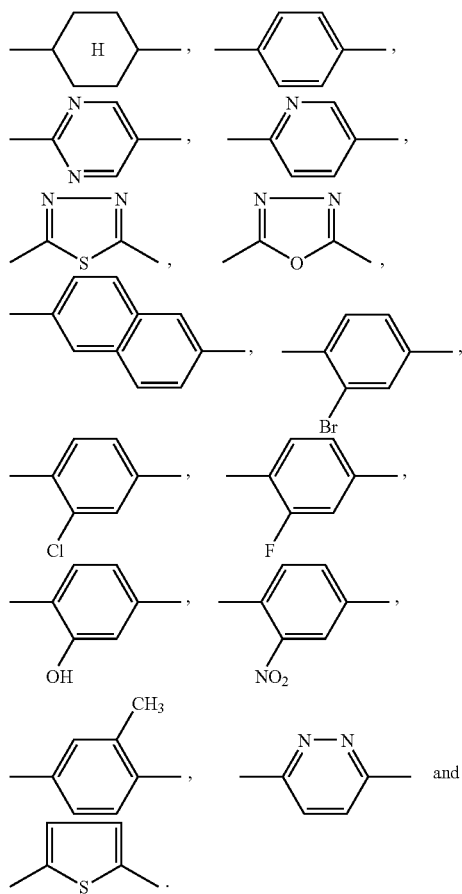

5. The compound as claimed in claim 1, wherein, in the groups $R^1$ and $R^2$, m is, in each cases 0; $Y^3$ is a single chemical bond; and $Y^4$ corresponds to —O—, —CO—O—, —O—CO—O— or —(R)N—CO—O—; and wherein the variable $Y^4$ for group $R^1$ is may be identical to, or different from, the variable $Y^4$ for group $R^2$.

6. A compound as claimed in claim 3, wherein T is selected from the group consisting of:

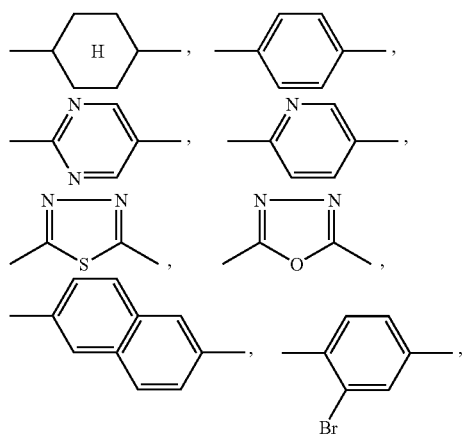
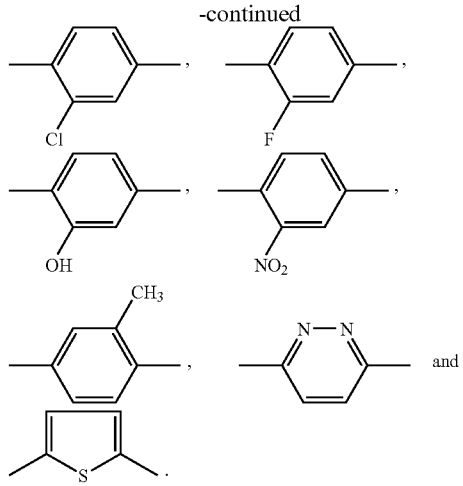

7. The compound as claimed in claim 2, wherein, the groups $R^1$ and $R^2$, m is, in each case, 0; $Y^3$ is a single chemical bond; and $Y^4$ corresponds to —O—, —CO—O—, —O—CO—O— or —(R)N—CO—O—; and wherein the variable $Y^4$ for group $R^1$ is identical to, or different from, the variable $Y^4$ for group $R^2$.

8. A liquid-crystalline composition, comprising at least one chiral compound of the general formula I, as claimed in claim 1, and one or more liquid crystalline materials.

9. A method for preparing an optical component, comprising forming said optical component from the composition of claim 8.

10. An optical component produced from the composition as claimed in claim 8.

11. A method of altering the optical properties of a liquid crystalline system, comprising contacting the compound as claimed in claim 1, as chiral dopant, with one or more liquid-crystalline systems.

12. A polymerizable liquid-crystalline compositions, comprising at least one chiral compound of the general formula I, as claimed in claim 1, and one or more polymerizable liquid crystalline materials.

13. A method of printing or coating a substrate, comprising applying the composition of claim 12 to a substrate.

14. A printed or coated substrate produced from the composition as claimed in claim 12.

15. A method of preparing a dispersion or emulsion, comprising contacting the composition of claim 12 with one or more solvents.

16. A dispersion or emulsion prepared from the composition as claimed in claim 12.

17. A method of preparing a film, comprising polymerizing the composition as claimed in claim 12.

18. A film produced from the composition as claimed in claim 12.

19. A method of preparing a pigment, comprising polymerizing the composition, as claimed in claim 12, within the interspace of a mesh.

20. A pigment prepared from the composition as claimed in claim 12.

* * * * *